US009022976B2

(12) United States Patent
Tegg

(10) Patent No.: US 9,022,976 B2
(45) Date of Patent: May 5, 2015

(54) PUSH-COIL STEERING MECHANISM

(71) Applicant: Troy T. Tegg, Elk River, MN (US)

(72) Inventor: Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/663,569

(22) Filed: Oct. 30, 2012

(65) Prior Publication Data

US 2014/0121595 A1 May 1, 2014

(51) Int. Cl.
*A61M 31/00* (2006.01)
*A61B 1/00* (2006.01)

(52) U.S. Cl.
CPC .................................. *A61B 1/00133* (2013.01)

(58) Field of Classification Search
CPC .................... A61M 25/0147; A61M 25/0136; A61M 25/0133
USPC ......... 604/95.04, 528, 95.01–95.03; 600/585, 600/146
See application file for complete search history.

(56) References Cited

U.S. PATENT DOCUMENTS

| | | | |
|---|---|---|---|
| 5,456,664 A * | 10/1995 | Heinzelman et al. | 604/528 |
| 5,626,553 A | 5/1997 | Frassica | |
| 7,269,453 B2 * | 9/2007 | Mogul | 600/374 |
| 7,749,247 B2 | 7/2010 | Tegg | |
| 8,021,327 B2 | 9/2011 | Selkee | |
| 8,137,308 B2 * | 3/2012 | Schultz | 604/95.04 |
| 2007/0232858 A1 * | 10/2007 | Macnamara et al. | 600/149 |
| 2008/0287862 A1 | 11/2008 | Weitzner et al. | |
| 2012/0029334 A1 * | 2/2012 | Tegg | 600/373 |
| 2012/0143088 A1 * | 6/2012 | Schultz | 600/585 |

FOREIGN PATENT DOCUMENTS

| | | |
|---|---|---|
| EP | 0521595 | 5/1999 |
| EP | 1607119 | 3/2009 |
| WO | 97/28839 | 8/1997 |

OTHER PUBLICATIONS

International Search Report and Written Opinion in PCT Application No. PCT/US2013/064353 (Jan. 21, 2014).

* cited by examiner

*Primary Examiner* — Theodore Stigell
*Assistant Examiner* — Benjamin Koo
(74) *Attorney, Agent, or Firm* — Dykema Gossett PLLC

(57) ABSTRACT

A handle assembly is provided for use in navigating a deformable shaft within a body. The assembly includes a first guide member defining first and second linear channels and a second guide member configured for rotation relative to the first guide member. First and second connectors are disposed within, and movable within, the first and second linear channels along first and second parallel axes, respectively, and are configured for coupling to first and second steering wires, respectively. The assembly includes means, such as a flexible coupling connected to the second guide member and the connectors, for translating rotation of the second guide member into linear movement of the first connector in a first axial direction and linear movement of the second connector in a second axial direction, opposite the first axial direction such that the first and second steering wires move in opposite directions.

22 Claims, 8 Drawing Sheets

PUSH-COIL STEERING MECHANISM

BACKGROUND OF THE INVENTION a. Field of the Invention

This invention relates to introducer sheaths, catheters and other devices configured to be maneuvered through a body. In particular, the invention relates to an improved handle assembly for use in navigating a deformable shaft of such a device within a body.

b. Background Art

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

Maneuvering a catheter or sheath through the body requires precise control for effective diagnosis and treatment and patient safety. Conventional catheters and sheaths include a deformable shaft or body and one more steering wires that extend from a proximal end of the shaft to a distal end of the shaft. A handle is coupled to the proximal end of the shaft and includes means for pulling and/or pushing the steering wires to place them under compression or tension in order to control translation and deflection of the distal tip of the shaft. In one conventional handle, a pair of steering wires are coupled to diametrically opposite points on a rotatable body controlled by the physician. Rotation of the body causes movement of the steering wires. To allow for a sufficient range of movement of the steering wires, the wires must be coupled to the rotating body at a relatively large distance from the center of the rotating body. As a result, the wires must be bent at relatively sharp angles proximal and distal to the rotating body as they assume a substantially more linear orientation relative to the body of the catheter or sheath. Bending of the wires leads to an increase in friction between the wires and surfaces engaged by the wires within the catheter or sheath and increases the chance that a steering wire will break.

The inventor herein has recognized a need for a handle assembly for use in navigating a deformable shaft of a medical device within a body that will minimize and/or eliminate one or more of the above-identified deficiencies.

BRIEF SUMMARY OF THE INVENTION

The present disclosure relates to a handle assembly for use in navigating a deformable shaft of a medical device within a body. In particular, the present disclosure relates to a handle assembly that is able to translate rotational motion into linear motion of steering wires while allowing the steering wires to remain in a substantially linear orientation throughout their length.

A handle assembly in accordance with one embodiment of the invention for use in navigating a deformable shaft of a medical device within a body, the handle assembly having a proximal end and a distal end, includes a first guide member disposed near the proximal end. The first guide member defines first and second linear channels. The assembly further includes a second guide member disposed distally of the first guide member and configured for rotation relative to the first guide member. The second guide member defines a circular channel in communication with the first and second linear channels. The assembly further includes a first connector disposed within the first linear channel and movable within the first linear channel along a first axis. The first connector is configured for coupling to a first steering wire. The assembly further includes a second connector disposed within the second linear channel and movable within the second linear channel along a second axis parallel to the first axis. The second connector is configured for coupling to a second steering wire. The assembly further includes a flexible coupling connected at a first end to the first connector and at a second end to the second connector. The flexible coupling extends from the first linear channel into the circular channel and from the circular channel into the second linear channel. The flexible coupling is connected to the second guide member for rotation therewith. Rotation of the second guide member causes movement of the first end of the flexible coupling in a first axial direction along the first axis and movement of the second end of the flexible coupling in a second axial direction, opposite the first axial direction, along the second axis such that the first and second steering wires move in opposite directions.

A handle assembly in accordance with another embodiment of the invention for use in navigating a deformable shaft of a medical device within a body, the handle assembly having a proximal end and a distal end, includes a first guide member disposed near the proximal end. The first guide member defines first and second linear channels. The assembly further includes a second guide member disposed distally of the first guide member and configured for rotation relative to the first guide member. The assembly further includes a first connector disposed within the first linear channel and movable within the first linear channel along a first axis. The first connector is configured for coupling to a first steering wire. The assembly further includes a second connector disposed within the second linear channel and movable within the second linear channel along a second axis parallel to the first axis. The second connector is configured for coupling to a second steering wire. The assembly further includes means for translating rotation of the second guide member into linear movement of the first connector in a first axial direction along the first axis and linear movement of the second connector in a second axial direction, opposite the first axial direction, along the second axis such that the first and second steering wires move in opposite directions.

A medical device handle in accordance with another embodiment of the invention includes a flexible coupling arcuately moveable with rotation of a manipulateable actuator. The handle further includes an angular-to-linear transformation guide having at least one channel contoured to direct a first portion of the flexible coupling from its arcuate path to a first substantially linear path oriented longitudinally through the medical device handle. The handle further includes a first steering wire coupled to the first portion of the flexible coupling that is oriented longitudinally through the medical device handle, and directed longitudinally through a distal end of the medical device handle.

A handle assembly in accordance with the present teachings represents an improvement relative to conventional handles because it allows the use of a rotational actuator for controlling linear movement of the steering wires in a medical device while doing so in a way that maintains a substantially linear orientation of the steering wires. As a result, the handle assembly prevents undesirable friction between the steering wires and other surfaces in the medical device and reduces the risk that a steering wire will break.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
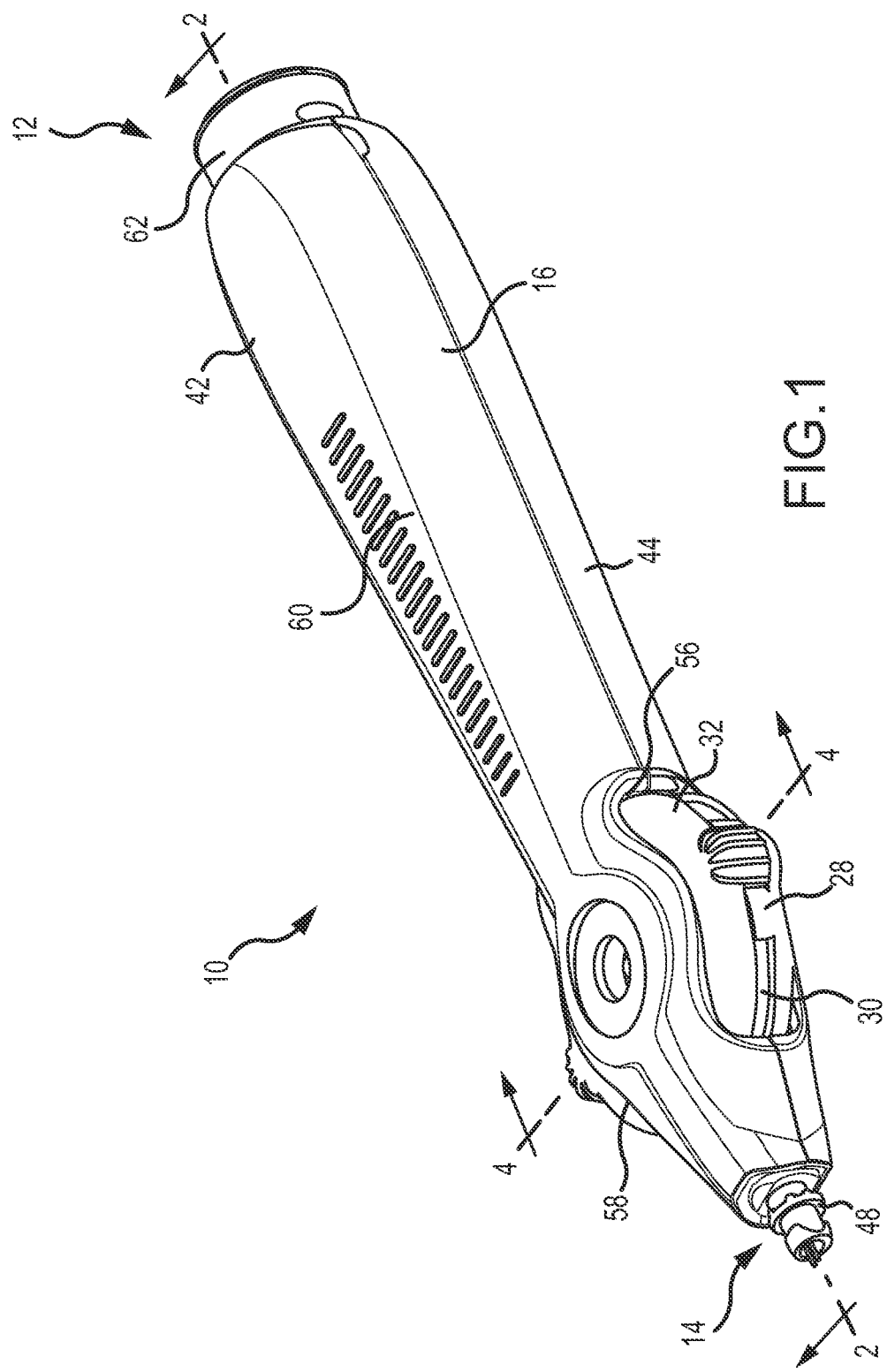
FIG. 1 is a perspective of a handle assembly invention for use in navigating a deformable shaft of a medical device within a body in accordance with one embodiment of the present teachings.
Figure 2:
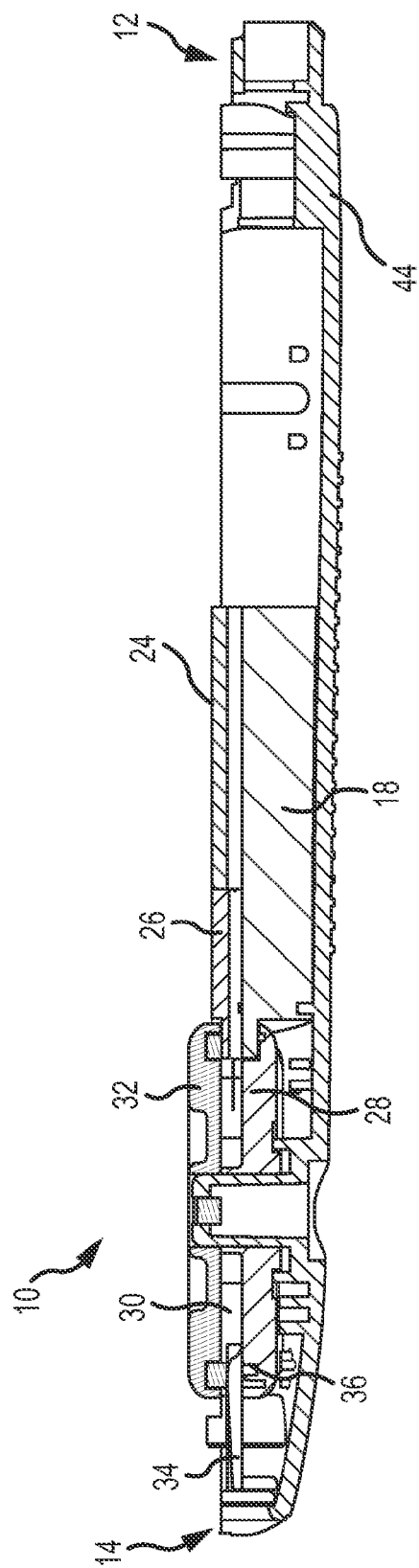
FIG. 2 is a cross-sectional view of the handle assembly of FIG. 1 taken along lines 2-2.
Figure 3:
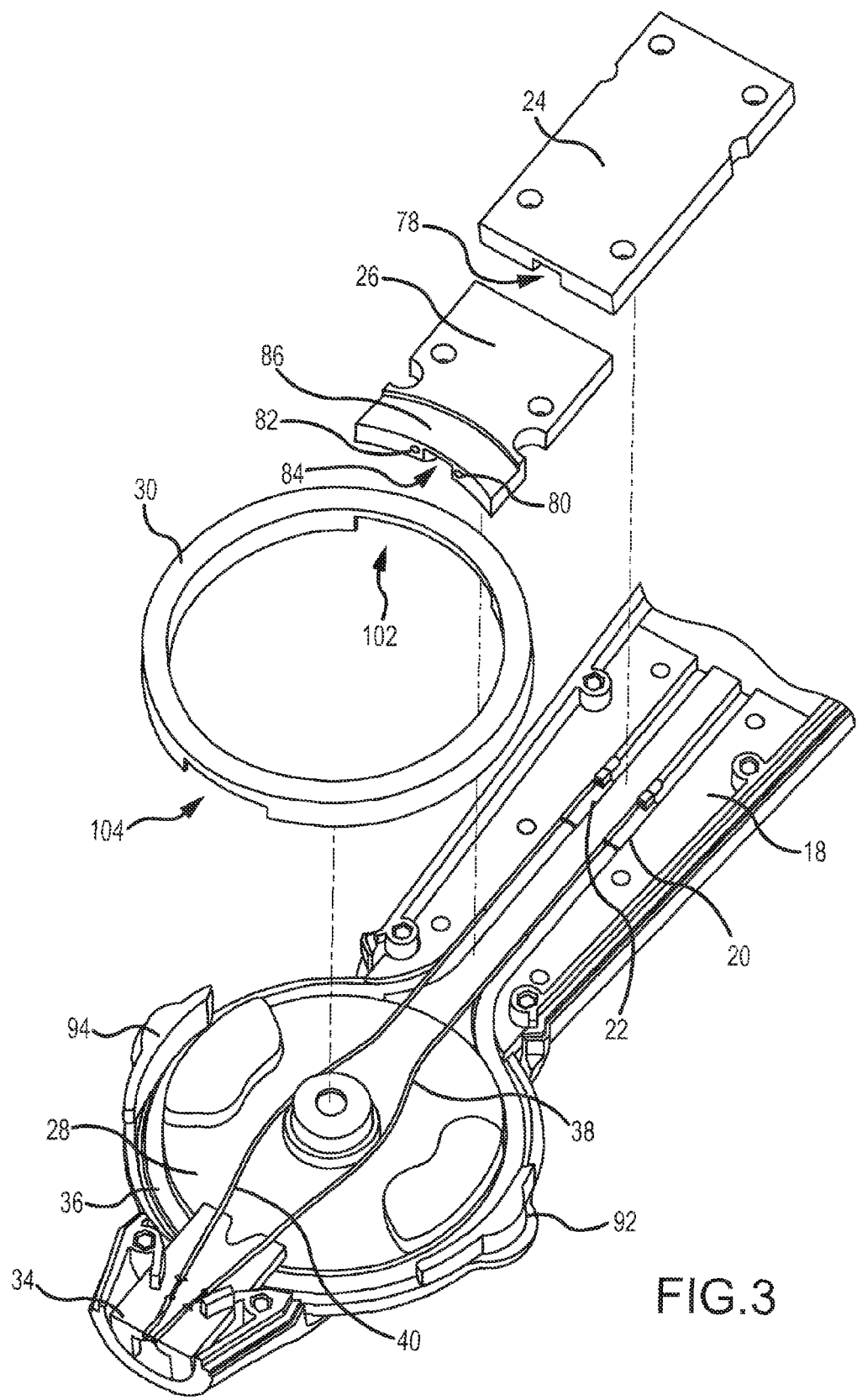
FIG. 3 is an exploded view of a portion of the handle assembly of FIG. 1.

Referring now to the drawings wherein like reference numerals are used to identify identical components in the various views, FIGS. 1-3 illustrate one embodiment of a handle assembly 10 for use in navigating a deformable shaft (not shown) of a medical device within a body. The medical device may comprise, for example, a catheter (such an electrophysiological (EP) mapping catheter or an ablation catheter used in diagnosis or treatment of cardiac tissue within the body) or an introducer sheath. It should be understood, however, that a handle assembly 10 in accordance with the present teachings may find application in connection with a wide variety of medical devices used within body for diagnosis or treatment. The deformable shaft of the medical device is typically an elongate, flexible, tubular member configured for movement within the body. The shaft may be made from conventional materials such as polyurethane and defines one or more lumens configured to house and/or transport electrical conductors, fluids, or surgical tools. The shaft may support electrodes and position sensors, associated conductors, and possibly additional electronics used for signal processing or conditioning. The shaft may also permit transport, delivery, and/or removal of fluids (including irrigation fluids and bodily fluids), medicines, and/or surgical tools or instruments. Assembly 10 has a proximal end 12 and a distal end 14. As used herein, "proximal" refers generally to a direction toward the end of the medical device nearer the clinician and further from the region of interest in the body where diagnosis or treatment takes place (generally inside the body of a patient), and "distal" refers to the end of the medical device further away from the clinician and nearer to the region of interest where diagnosis or treatment takes place. In the case of assembly 10, in particular, the distal end 14 comprises the end that is connected to the deformable shaft of the medical device. Assembly 10 may include a housing 16, guide member 18, connectors 20, 22, cover 24, steering wire guide member 26, guide member 28, retaining ring 30, cover 32, steering wire guide member 34, and means, such as flexible coupling 36, for translating rotation of guide member 28 into linear movement of connectors 20, 22, and steering wires 38, 40 coupled thereto in opposite axial directions.

Figure 4:
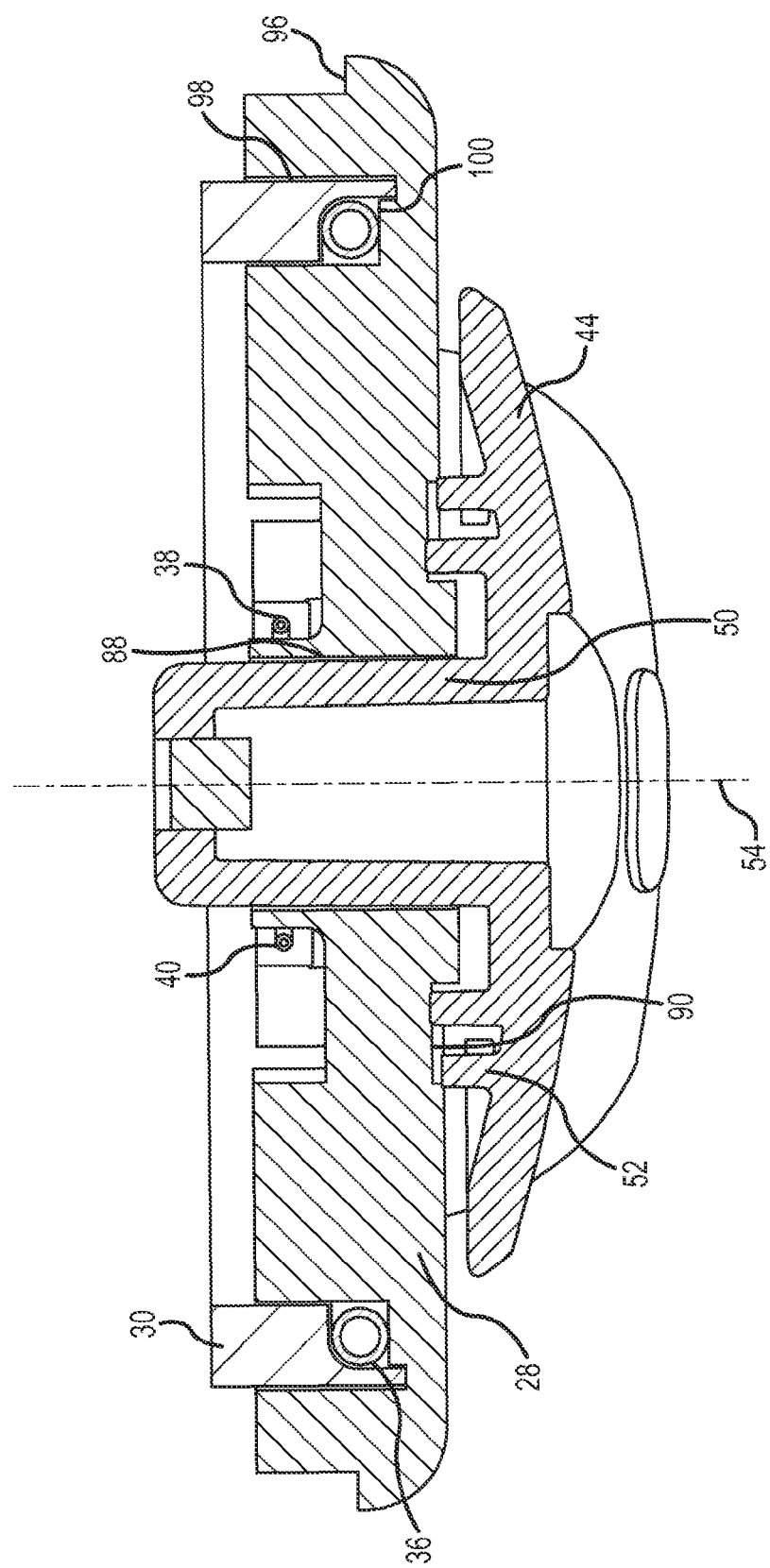
FIG. 4 is a cross-sectional view of the handle assembly of FIG. 1 taken along lines 4-4.

Referring to FIG. 1, housing 16 provides structural support to the other components of assembly 10 and protection against external elements and objects. Housing 16 may be made from conventional plastics. In the illustrated embodiment, housing 16 may include upper and lower members 42, 44 that may be located relative to one another by aligning corresponding pins (not shown) and receptacles 46 (see FIG. 6) and may be coupled to one another through a press fit relationship. It should be understood, however, that members 42, 44 could be coupled together using a variety of conventional fasteners including screws, welds, or adhesives. Housing 16 may define a circular mount 48 at distal end 14 to which the deformable shaft of the medical device may be coupled and through which steering wires 38, 40 may be directed longitudinally through the distal end 14 of assembly 10 into the shaft. Referring to FIG. 4, a portion of member 44 of housing 16 intermediate ends 12, 14 of assembly 10 may define a cylindrical center post 50 and one or more circular rails 52 configured to support guide member 28 for rotation about a rotational axis 54. Referring again to FIG. 1, housing 16 may further define aligned openings 56, 58 on either side and intermediate ends 12, 14 through which guide member 28, ring 30 and cover 32 may extend. Housing 16 may further define a surface 60 intermediate ends 12, 14 and proximal to openings 56, 58 configured to be gripped by a hand. Housing 16 may further define a connector or interface 62 at proximal end 12 that provides mechanical, fluid/or and electrical connection(s) for conduits or cables extending from, for example, a fluid source (not shown) having a biocompatible fluid such as saline for irrigation or an ablation generator (not shown) for delivery of RF ablation energy.

Figure 5:
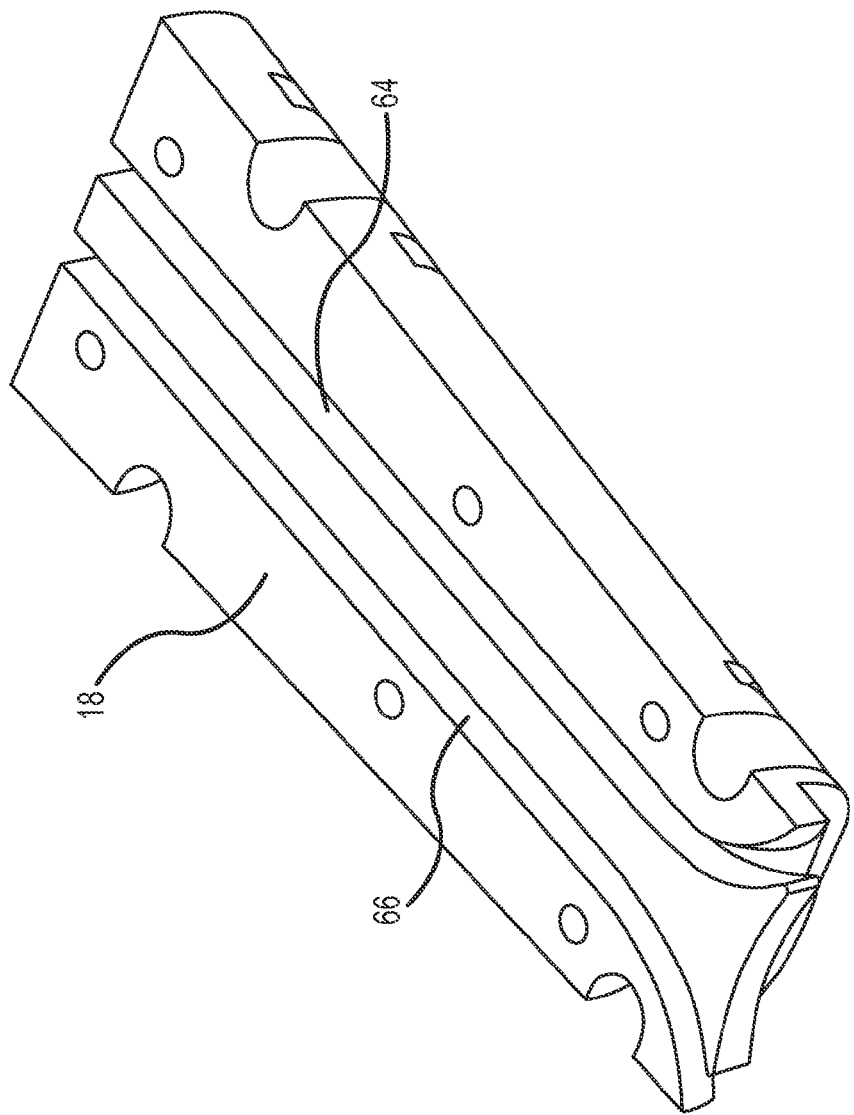
FIG. 5 is an enlarged perspective view of a guide member of the handle assembly of FIG. 1.
Figure 6:
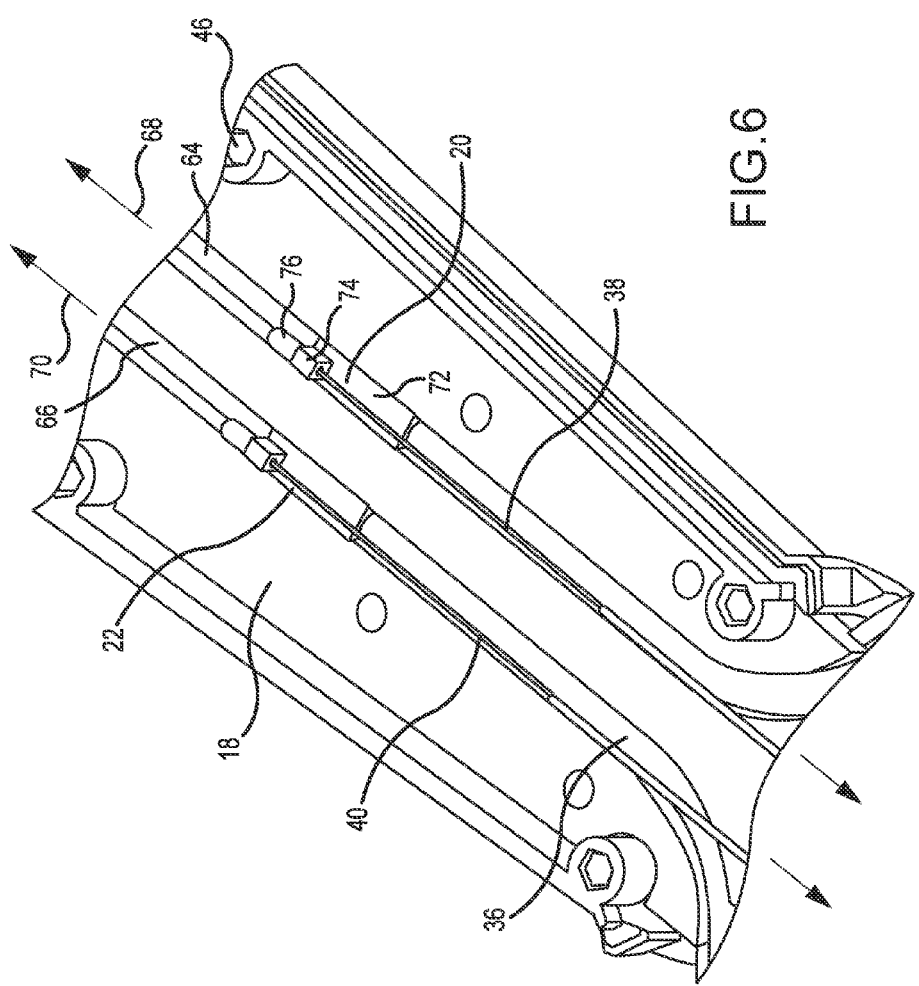
FIG. 6 is an enlarged perspective view of a portion of the handle assembly of FIG. 1.

Referring now to FIG. 3, guide member 18 guides movement of connectors 20, 22 along defined paths in response to an external force acting upon connectors 20, 22. Member 18 may be made from conventional plastics and is configured to be received within member 44 of housing 16 near proximal end 12 of assembly 10. Referring to FIG. 5, member 18 defines a pair of linear channels 64, 66 that extend from a proximal end of member 18 to a distal end of member 18 and that are, in the illustrated embodiment, parallel to one another over a portion of the length of guide member 18. As used herein, "linear" indicates that at least a portion of each of the channels 64, 66 is substantially straight such that connectors 20, 22 can move in a straight line within that portion of each channel 64, 66. As shown in the illustrated embodiments, channels 64, 66 may curve away from one another proximate a distal end of guide member 18 for a purpose described hereinbelow. Referring to FIG. 6, channels 64, 66, guide connectors 20, 22 back and forth along axes 68, 70. Axes 68, 70 may be parallel to one another and contained in a common plane which may be perpendicular to rotational axis 54. In the illustrated embodiment, each of channels 64, 66 is shaped complementary to connectors 20, 22 and includes a bottom wall and a pair of side walls extending perpendicular to the bottom wall. It should be understood, however, that the shape of channels 64, 66 may vary depending on the desired shape of connectors 20, 22.

Connectors 20, 22 are provided to couple steering wires 38, 40 to portions of the flexible coupling 36 that are oriented longitudinally through assembly 10 for a purpose described hereinbelow. Connectors 20, 22 are disposed within channels 64, 66 in guide member 18 and are configured to move within channels 64, 66 along axes 68, 70. Each of connectors 20, 22 includes a lower portion 72 sized to be received within a corresponding channel 64, 66 and configured for connection to one end of coupling 36. Coupling 36 may be coupled to connectors 20, 22 at the distal end of lower portion 72 or may extend partially or entirely through lower portion 72 provided that the end of coupling 36 is secured against movement relative to connector 20, 22. Coupling 36 may be fixed to connectors 20, 22 using conventional fasteners such as adhesives or through a press fit relationship. Each of connectors 20, 22 further includes an upper portion 74 that may be disposed outside of a corresponding channel 62, 64 and is configured for connection to one of steering wires 38, 40. Wires 38, 40 may extend through upper portion 74 for connection to a solder cup 76, crimp sleeve or other wire locking mechanism. Although a particular structure for connectors 20, 22 is shown in the illustrated embodiment, it should be understood that the composition, shape and size of connectors 20, 22 may vary provided the connector is capable of coupling to both one end of coupling 36 and to a corresponding steering wire 38, 40.

Referring again to FIG. 3, cover 24 encloses at least a portion of channels 64, 66 and prevents movement of connectors 20, 22 or coupling 36 out of channels 64, 66 when wires 38, 40 are placed under compression or tension. Cover 24 may be coupled to guide member 18 using conventional fasteners such as, for example, screws, adhesives, snap-fin pins and other plastic pins, etc. Cover 24 may also define a channel 78 extending from a proximal end of cover 24 to a distal end of cover 24 configured for passage of fluids and/or conductors.

Steering wire guide member 26 guides wires 38, 40 from connectors 20, 22 towards guide member 28. Similar to cover 24, member 26 may also enclose a portion of channels 64, 66 to thereby prevent movement of connectors 20, 22 or coupling 36 out of channels 64, 66 when wires 38, 40 are placed under compression or tension. Member 26 may be coupled to guide member 18 using conventional fasteners such as, for example, screws, adhesives, snap-fit pins and other plastic pins, etc. Member 26 defines a pair of bores 80, 82 extending from a proximal end of member 26 to a distal end of member 26 through which steering wires 38, 40 extend. Member 26 may also define a channel 84 extending between bores 80, 82 from a proximal end of member 26 to a distal end of member 26 configured for passage of fluids and/or connectors. Channel 84 may be aligned with, and in communication with, channel 78 in cover 24. A distal end of guide member 26 defines an arcuate ledge 86 configured to receive a portion of retaining ring 30 thereon.

Guide member 28 comprises a manipulateable (and, in particular, rotatable) actuator providing a means for a physician to control movement of coupling member 36 and, as a result, connectors 20, 22 and steering wires 38, 40. Member 28 is disposed distally of guide member 18. Referring again to FIG. 4, member 28 is supported within housing 16 on post 50 and rails 52 for rotation relative to guide member 18. In particular, member 28 includes a central opening sized to receive post 50. A circular wall or projection 88 extends axially from one side of member 28 and defines a portion of the central opening. Steering wires 38, 40 traverse member 28 and are disposed on diametrically opposite sides of projection 88. Member 28 defines one or more circular grooves 90 on an opposite side of member 28 configured to receive rails 52. Referring to FIG. 1, member 28 projects outwardly through openings 56, 58 in housing 16. Referring to FIG. 3, member 28 defines diametrically opposed flanges 92, 94 that may be used by a physician to rotate member 28 (using, for example, a thumb or finger). Referring again to FIG. 4, member 28 further defines a ledge 96 about its radially outer periphery configured to receive cover 32. Member 28 further defines a circular channel 98 configured to receive ring 30 and coupling 36. Channel 98 is aligned with linear channels 64, 66 in guide member 18 such that circular channel 98 is in communication with linear channels 64, 66. Members 18, 28 therefore combine to form an angular-to-linear transformation guide with a continuous channel 64, 98, 66 contoured to direct portions of coupling 36 from accurate paths in channel 98 to substantially linear path in channels 64, 66 that are oriented longitudinally through handle assembly 10. As shown in the illustrated embodiment, the depth of channel 98 may vary to define a shoulder 100.

Retaining ring 30 is provided to retain coupling 36 in place within channel 98 while also permitting steering wires 38, 40 to traverse guide member 28 from steering wire guide member 26 to the deformable shaft of the medical device. Ring 30 is configured to be received within channel 98. Referring to FIG. 4, ring 30 may form a curved recess in a radially inner surface configured to receive coupling 36. Ring 30 therefore inhibits movement of coupling 36 in one direction parallel to axis 54 (the bottom of channel 98 inhibits movement of coupling 36 in the opposite direction parallel to axis 54) and also in a radially outward direction (the radially inner wall of channel 98 inhibits movement of coupling 36 in a radially inward direction). A radially outer portion of ring 30 may be disposed between the radially outer wall of channel 98 and shoulder 100 to position ring 30 within channel 98. Referring to FIG. 3, ring 30 further defines diametrically opposed openings 102, 104 configured to allow passage of steering wires 38, 40. Opening 102 is sized to receive a distal end of steering wire guide member 26 such that ring 30 is supported on ledge 86 of member 26. Similarly, opening 104 is sized to receive a proximal end of steering wire guide member 34.

Referring again to FIGS. 1-2, cover 32 prevents foreign objects and elements from interfering with the operation of coupling 36 and steering wires 38, 40. Cover 32 defines a central opening configured to receive post 50 of member 44. Cover 32 is also sized to be received on ledge 96 of member 28 and is configured for rotation with member 28. Cover 32 projects outwardly through openings 56, 58 of housing 16 and is restrained from axial movement along rotational axis 54 by member 42 of housing 16.

Figure 7:
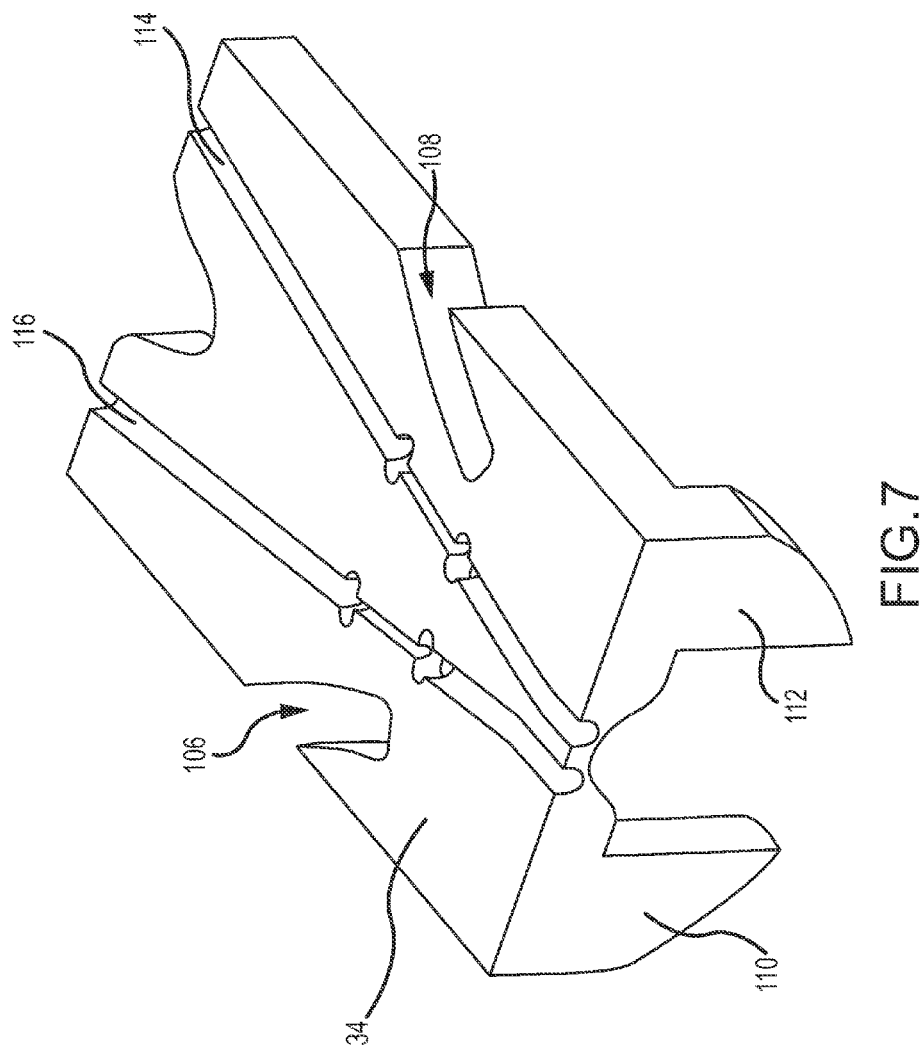
FIG. 7 is an enlarged perspective view of a guide member of the handle assembly of FIG. 1.

Steering wire guide member 34 guide wires 38, 40 towards the opening in mount 48 and, therefore, to the deformable shaft of the medical device. Member 34 is disposed distally of guide member 28 proximate distal end 14 of assembly 10. Referring to FIG. 7, member 34 may define a notch 106, 108 on either side configured to receive corresponding projections in member 44 of housing 16 and a pair of downwardly projecting flanges 110, 112 configure to engagement corresponding surfaces in housing 16 in order to limit movement of member 34 relative to housing 16. Member 34 further defines grooves 114, 116 extending from a proximal end of said member 34 to a distal end of member 34 and configured to receive steering wires 38, 40. A distance between the grooves 114, 116 is greater at the proximal end of member 34 than at the distal end of member 34 in order to bring wires 38, 40 closer together prior to entry into the deformable shaft of the medical device.

Figure 8:
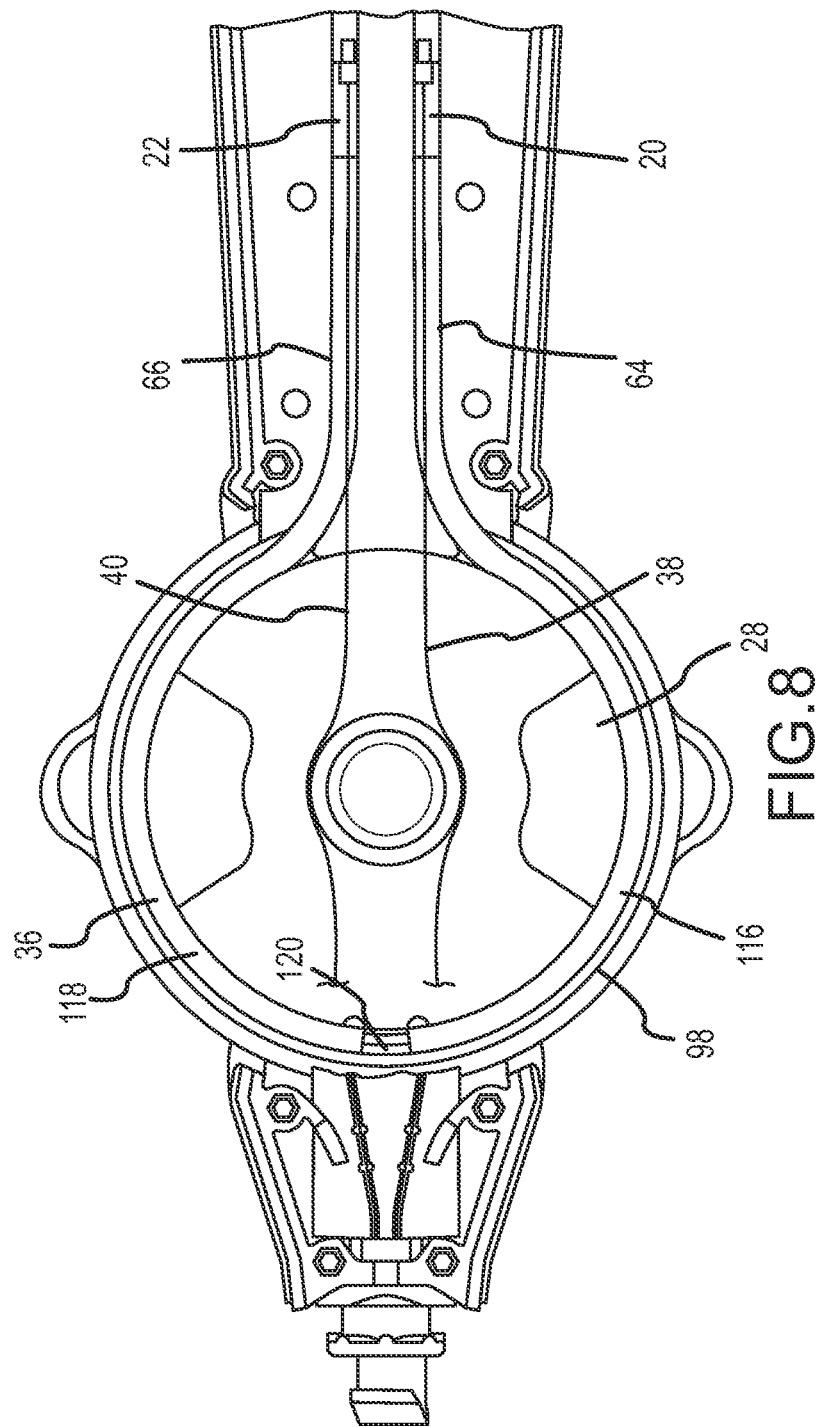
FIG. 8 is a plan view of a portion of the handle assembly of FIG. 1.

Referring to FIG. 8, flexible coupling 36 provides a means for translating rotation of guide member 28 into linear movement of connectors 20, 22, and steering wires 38, 40 in opposite axial directions. Coupling 36 may comprise a spring or coil that is resistant to compression in one direction to enable one of steering wires 38, 40 to be pushed. In another representative embodiment coupling 36 includes a spring or coil resistant to appreciable compression while enabling stretching in tension to thereby allow assembly 10 to take up slack (if any) when the tip of the medical device is deflected. Coupling 36 is connected at a first end to connector 20 and at a second end to connector 22. Coupling 36 extends from linear channel 64 in guide member 18 into circular channel 98 of guide member 28 and from circular channel 98 into linear channel 66 of guide member 18. Coupling 36 is connected to guide member 28 for rotation therewith and is therefore arcuately movable with rotation of guide member 28. In the illustrated embodiment, coupling 36 comprises two flexible members, such as cables 116, 118, with each member coupled at one end to a corresponding connector 20, 22 and another end connected to a common spacer 120. The spacer 120 is fixed to guide member 28 such that rotation of guide member 28 causes corresponding movement of spacer 120 and cables 116, 118. It should be understood, however, that a single flexible member such as a cable could alternatively be used having one end coupled to one of connectors 20, 22 and an opposite end coupled to the other of connectors 20, 22. The cable would be fixed to guide member 28 at one or more points (e.g. through the use of an adhesive or a clamp) such that rotation of guide member 28 would cause corresponding movement of the cable. Rotation of guide member 28 causes movement of one end of coupling 36—and therefore connector 20—in one axial direction along axis 68. At the same time, the other end of coupling 36—and therefore connector 22—is caused to move in the opposite axial direction along axis 70. By virtue of the movement of connectors 20, 22, steering wires 38, 40 move in opposite axial directions causing wires 38, 40 to extend or retract relative to distal end 14 of handle assembly 10. In this manner, coupling 36 translates the rotational or angular movement of guide member 28 into linear movement of steering wires 38, 40 thereby enabling deflection of the distal tip of the medical device. Moreover, assembly 10 translates this motion in a manner such that steering wires 38, 40 may remain in a substantially linear orientation within housing 16 thereby reducing friction of wires 38, 40 against surfaces within housing 16 and the potential that a wire 38, 40 will break. Although flexible coupling 36 has been described herein as comprising one or more cables, it should be understood that other types of flexible coupling may alternatively be used.

A handle assembly 10 in accordance with the present teachings represents an improvement relative to conventional handles because, among other things, it allows the use of a rotational actuator such as guide member 28 for controlling linear movement of the steering wires 38, 40 in a medical device while doing so in a way that maintains a substantially linear orientation of the steering wires 38, 40. As a result, the handle assembly 10 prevents undesirable friction between the steering wires 38, 40 and other surfaces in the medical device and reduces the risk that a steering wire will break.

The medical device steering technology described herein may be implemented in a variety of apparatuses, systems, and/or methods. For example, one representative method facilitates deflection of a distal segment of a flexible medical device operated at least in a part by a connected handle. Angular displacement of at least one flexible member in the handle may be converted to linear displacement of at least one linearly-actuated member, and a steering wire(s) respectively coupled to the linearly-actuated member may be moved substantially longitudinally through the handle in response to the angular displacement. In this manner, an angular manipulation of a deflection actuator can cause deflection of the distal segment of the medical device without unnecessarily compromising the structural integrity of the steering wire(s).

Although several representative embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A handle assembly for use in navigating a deformable shaft of a medical device within a body, said handle assembly having a proximal end and a distal end and said handle assembly comprising:

the distal end of the handle assembly connected to the deformable shaft of the medical device;

a first guide member disposed near said proximal end, said first guide member defining first and second linear channels;

a second guide member disposed distally of said first guide member and configured for rotation relative to said first guide member, said second guide member defining a circular channel in communication with said first and second linear channels;

a first connector disposed within said first linear channel and movable within said first linear channel along a first axis, said first connector configured for coupling to a first steering wire;

a second connector disposed within said second linear channel and movable within said second linear channel along a second axis parallel to said first axis, said second connector configured for coupling to a second steering wire; and a flexible coupling comprising a first end abutting said first connector and a second end abutting said second connector, said flexible coupling extending from said first linear channel into said circular channel, said flexible coupling connected to said second guide member for rotation therewith, wherein rotation of said second guide member causes movement of said first end of said flexible coupling and said first connector in a first axial direction along said first axis and movement of said second end of said flexible coupling and said second connector in a second axial direction, opposite said first axial direction, along said second axis such that said first and second steering wires move in opposite directions.

2. The handle assembly of claim 1, further comprising a retainer ring configured to be received within said circular channel, said retainer ring retaining said flexible coupling within said circular channel.

3. The handle assembly of claim 2 wherein said retainer ring defines first and second diametrically opposed openings configured for passage of said first and second steering wires therethrough.

4. The handle assembly of claim 1 wherein said flexible coupling includes first and second members and a spacer disposed between said first and second members, said spacer affixed to said second guide member.

5. The handle assembly of claim 1, further comprising a third guide member coupled to said first guide member and covering at least a portion of said first and second linear channels, said third guide member defining first and second bores configured to receive said first and second steering wires.

6. The handle assembly of claim 1, further comprising a third guide member disposed distally of said second guide member, said third guide member defining first and second grooves extending from a proximal end of said third guide member to a distal end of said third guide member and configured to receive said first and second steering wires.

7. The handle assembly of claim 6 wherein a distance between said first and second grooves is greater at said proximal end of said third guide member than at said distal end of said third guide member.

8. The handle assembly of claim 1 wherein said second guide member is configured for rotation about a rotational axis extending perpendicular to a plane containing said first and second axes.

9. The handle assembly of claim 1 wherein said second guide member includes a projection centered about an axis of rotation for said second guide member, said first and second steering wires disposed on diametrically opposite sides of said projection.

10. A handle assembly for use in navigating a deformable shaft of a medical device within a body, said handle assembly having a proximal end and a distal end and said handle assembly comprising:
the distal end of the handle assembly connected to the deformable shaft of the medical device;
a first guide member disposed near said proximal end, said first guide member defining first and second linear channels;
a second guide member disposed distally of said first guide member and configured for rotation relative to said first guide member;
a first connector disposed within said first linear channel and movable within said first linear channel along a first axis, said first connector configured for coupling to a first steering wire;
a second connector disposed within said second linear channel and movable within said second linear channel along a second axis parallel to said first axis, said second connector configured for coupling to a second steering wire; and
means for translating rotation of said second guide member into linear movement of said first connector in a first axial direction along said first axis and linear movement of said second connector in a second axial direction, opposite said first axial direction, along said second axis such that said first and second steering wires move in opposite directions.

11. The handle assembly of claim 10 wherein said translating means comprises a flexible coupling connected at a first end to said first connector and at a second end to said second connector, said flexible coupling extending from said first linear channel into a circular channel in said second guide member, said circular channel in communication with said first and second linear channels, and from said circular channel into said second linear channel, said flexible coupling connected to said second guide member for rotation therewith.

12. The handle assembly of claim 11, further comprising a retainer ring configured to be received within said circular channel, said retainer ring inhibiting movement of said flexible coupling in a direction parallel to a rotational axis of said second guide member.

13. The handle assembly of claim 12 wherein said retainer ring defines first and second diametrically opposed openings configured for passage of said first and second steering wires therethrough.

14. The handle assembly of claim 11 wherein said flexible coupling includes first and second members and a spacer disposed between said first and second members, said spacer affixed to said second guide member.

15. The handle assembly of claim 10, further comprising a third guide member coupled to said first guide member and covering at least a portion of said first and second linear channels, said third guide member defining first and second bores configured to receive said first and second steering wires.

16. The handle assembly of claim 10, further comprising a third guide member disposed distally of said second guide member, said third guide member defining first and second grooves extending from a proximal end of said third guide member to a distal end of said third guide member and configured to receive said first and second steering wires.

17. The handle assembly of claim 16 wherein a distance between said first and second grooves is greater at said proximal end of said third guide member than at said distal end of said third guide member.

18. The handle assembly of claim 10 wherein said second guide member is configured for rotation about a rotational axis extending perpendicular to a plane containing said first and second axes.

19. The handle assembly of claim 10 wherein said second guide member includes a projection centered about an axis of rotation for said second guide member, said first and second steering wires disposed on diametrically opposite sides of said projection.

20. A medical device handle, comprising:
a flexible coupling arcuately moveable with rotation of a manipulateable actuator;
an angular-to-linear transformation guide comprising at least one channel, the at least one channel being contoured to enable a first portion of the flexible coupling to be pushed along an arcuate path towards a proximal end of the medical device handle and to be pushed along a first substantially linear path oriented substantially parallel to a longitudinal axis of the medical device handle and towards the proximal end of the medical device handle; and
a first steering wire oriented longitudinally along the medical device handle, wherein the first steering wire is coupled to the first portion of the flexible coupling, and wherein linear motion of the first portion of the flexible coupling results in pulling of the first steering wire towards the proximal end of the medical device handle in response to rotation of the manipulateable actuator.

21. The medical device handle of claim 20 wherein the rotation of the manipulateable actuator causes the arcuate movement of the flexible coupling, which consequently causes the first steering wire coupled thereto to extend or retract relative to the distal end of the medical device handle depending on a direction of the rotation of the manipulateable actuator.

22. The medical device handle of claim 20, wherein the angular-to-linear transformation guide includes a second channel contoured to enable a second portion of the flexible coupling to be pushed from its arcuate path towards the proximal end of the medical device handle and to a second substantially linear path oriented longitudinally through the medical device handle, wherein the medical device handle further comprises a second steering wire coupled to the second portion of the flexible coupling and directed longitudinally through the distal end of the medical device handle, and wherein the second portion of the flexible coupling pulls the second steering wire towards the proximal end of the medical device handle in response to an opposite rotation of the manipulateable actuator.

* * * * *